US008778623B2

(12) United States Patent
Johnson et al.

(10) Patent No.: US 8,778,623 B2
(45) Date of Patent: Jul. 15, 2014

(54) COMPOSITIONS AND METHODS OF USING DIFFERENTIATED CELLS SENSITIZED TO BOTULINUM NEUROTOXIN

(71) Applicant: Wisconsin Alumni Research Foundation, Madison, WI (US)

(72) Inventors: Eric Arthur Johnson, Madison, WI (US); Regina Whitemarsh, Madison, WI (US); Sabine Pellett, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/779,972

(22) Filed: Feb. 28, 2013

(65) Prior Publication Data

US 2014/0080142 A1    Mar. 20, 2014

Related U.S. Application Data

(60) Provisional application No. 61/700,965, filed on Sep. 14, 2012.

(51) Int. Cl.
*A01N 1/02* (2006.01)
(52) U.S. Cl.
USPC ............................. 435/7.4; 435/70.3; 435/326
(58) Field of Classification Search
USPC .......................................... 435/70.3, 7.4, 326
See application file for complete search history.

(56) References Cited

U.S. PATENT DOCUMENTS

| | | | | |
|---|---|---|---|---|
| 6,106,824 | A * | 8/2000 | Kaplitt et al. | 424/93.2 |
| 6,495,513 | B1 * | 12/2002 | Rueger et al. | 514/8.3 |
| 6,683,108 | B1 * | 1/2004 | Baxter et al. | 514/443 |
| 6,949,505 | B1 * | 9/2005 | Rueger et al. | 514/8.4 |
| 2003/0185792 | A1 * | 10/2003 | Keck et al. | 424/85.1 |
| 2005/0255093 | A1 * | 11/2005 | Shone et al. | 424/94.4 |
| 2006/0078499 | A1 * | 4/2006 | Hen et al. | 424/9.2 |
| 2007/0054266 | A1 * | 3/2007 | Sato et al. | 435/6 |
| 2008/0160561 | A1 * | 7/2008 | Fernandez-Salas et al. | 435/29 |
| 2008/0227137 | A1 * | 9/2008 | Zhang et al. | 435/29 |
| 2010/0159595 | A1 * | 6/2010 | Zhang et al. | 435/377 |
| 2010/0319073 | A1 * | 12/2010 | Sockanathan et al. | 800/3 |
| 2011/0091927 | A1 * | 4/2011 | Reubinoff et al. | 435/29 |

FOREIGN PATENT DOCUMENTS

| | | | | |
|---|---|---|---|---|
| CA | 2619029 | * | 8/2009 | |
| WO | 2009/146098 | * | 12/2009 | C12N 5/08 |

OTHER PUBLICATIONS

Higashi, H. et al, Glycoconjugate Journal vol. 20, pp. 49-58, 2004, Ganglioside/protein kinase signals triggering cytoskeletal actin reorganization.*

Ling, Karen K.Y. et al, FEBS Letters, vol. 579, pp. 2469-2474, 2005, ATP potentiates the formation of AChR aggregate in the co-culture of NG108-15 cells with C2C12 myotubes.*

Pun, S et al, FEBS Letters, vol. 418, pp. 275-281, 1997, NG108-15 cells express neuregulin that induces AChR alpha-subunit synthesis in cultured myotubes.*

(Continued)

*Primary Examiner* — Albert Navarro
*Assistant Examiner* — Ginny Portner
(74) *Attorney, Agent, or Firm* — Quarles & Brady LLP

(57) ABSTRACT

Differentiated cholinergic cells having motor neuron-like morphology and increased sensitivity to botulinum neurotoxin are provided herein. Methods of using such differentiated cells for detecting neurotoxin are also provided.

18 Claims, 3 Drawing Sheets

(56) References Cited

OTHER PUBLICATIONS

Yamamuro, Yutaka et al, Life Sciences, vol. 86, pp. 839-843, 2010, Asymmetric regulation by estrogen at the cholinergic gene locus in differentiated NG108-15 cells.*
Choi, Roy C.Y et al, Neuroscience Letters, vol. 236, pp. 167-170, 1997, NG108-15 cells induce the expression of muscular acetylcholinesterase when co-cultured with myotubes.*
Nelson, Phillip et al, PNAS, vol. 73(1) pp. 123-127, Jan. 1976, Synapse formation between clonal neuroblastomaX glioma hybrid cells and striated muscule cells.*
Stacpoole, SRL et al, National Protoc. vol. 6(8), pp. 1229-1240, 2011.*
Kowtha, VC et al, Neuroscience Letters, vol. 164, pp. 129-133, 1993, Comparative electrophysicological properties of NG108-15 cells in serum containing and serum free media.*
Stanton, Benjamin Z et al, Molecular Biosystems, 2010, vol. 6, pp. 44-54, Small molecule modulators of the Sonic Hedgehog signaling pathway.*
Yamamoto, Takehiro et al, Journal of Biological Chemistry, 2005, vol. 280, pp. 16979-16986, Expression and Function of cGMP-dependent Protein Kinase Type 1 during Medaka Fish Embryogenesis.*
Tojima, Takuro et al, Neuroscience Research, vol. 37, 2000, pp. 153-161, Acquisition of neuronal proteins during differentiation of NG108-15 cells.*
Wichterle et al, Cell, Aug. 9, 2002, vol. 110, pp. 385-397, together with Supplemental Data (pp. 1-2), Directed Differentiation of Enbryonic Stem Cells into Motor Neurons.*
Zhang, Xiaodong et al, Brain Research 2006, vol. 1073-1074, pp. 109-119, Induction of neuronal differentiation of adult human olfactory neuroepithelial-derived progenitors.*
El-Akabawy, Gehan et al, Stem Cells and Development, vol. 20(11), 2011, published online Apr. 5, 2011, Purmorphamine Increases DARPP-32 Differentiation in Human Striatal Neural Stem Cells through the Hedgehog pathway.*
Burattini, et al., C2C12 Murine Myoblasts as a Model of Skeletal Muscle Development: Morpho-Functional Characterization, European Journal of Histochemistry, 2004, 48(3):223-234.
Busis, et al., Three Cholinergic Neuroblastoma Hybrid Cell Lines That Form Few Synapses on Myotubes are Deficient in Acetylcholine Receptor Aggregation Molecules and Large Dense Core Vesicles, Brain Research, 1984, 324(2):201-210.
Choi, et al., NG108-15 Cells Induce the Expression of Muscular Acetylcholinesterase When Co-Cultured with Myotubes, Neuroscience Letters, 1997, 236(3):167-170.
Dahms, et al., Ganglioside Composition is Regulated During Differentiation in the Neuroblastoma X Glioma Hybrid Cell Line NG108-15, The Journal of Neuroscience, 1983, 3(4):806-817.
Dong, et al., Synaptotagmins I and II Mediate Entry of Botulinum Neurotoxin B Into Cells, Journal of Cell Biology, 2003, 162(7):1293-1303.
Fernandez-Salas, et al., Botulinum Neurotoxin Serotype a Specific Cell-Based Potency Assay to Replace the Mouse Bioassay, PLoS ONE, 2012, 7(11):e49516, pp. 1-13.
Fischer, et al., Bimodal Modulation of the Botulinum Neurotoxin Protein-Conducting Channel, PNAS, 2009, 106 (5):1330-1335.
Fujii, et al., A CNS-Specific POU Transcription Factor, Brn-2, is Required for Establishing Mammalian Neural Cell Lineages, Neuron, 1993, 11(6):1197-1206.
Hatheway, Botulism, Chapter 12, Laboratory Diagnosis of Infectious Diseases, Springer-Verlag New York Inc., 1988, pp. 111-133.
Higashida, Acetylcholine Release by Bradykinin, Inositol 1,4,5-Trisphosphate and Phorbol Dibutyrate in Rodent Neuroblastoma Cells, Journal of Physiology, 1988, 397:209-222.
Holmgren, et al., Polystyrene-Adsorbed Gangliosides for Investigation of the Structure of the Tetanus-Toxin Receptor, Eur. J. Biochem., 1980, 106:371-379.
Jiang, et al., Muscle Induces Neuronal Expression of Acetylcholinesterase in Neuron-Muscle Co-Culture, The Journal of Biological Chemistry, 2003, 278(46):45435-45444.

Johnson, et al., Induction and Repression of Mammalian Achaete-Scute Homologue (MASH) Gene Expression During Neuronal Differentiation of P19 Embryonal Carcinoma Cells, Development, 1992, 114:75-87.
Li, et al., Directed Differentiation of Ventral Spinal Progenitors and Motor Neurons from Human Embryonic Stem Cells by Small Molecules, Stem Cells, 2008, 26:886-893.
Malizio, et al., Purification of Clostridium Botulinum Type A Neurotoxin, Methods in Molecular Biology, 2000, 145:27-39.
McGee, et al., Regulation of Acetylcholine Release from Neuroblastoma X Glioma Hybrid Cells, Proc. Natl. Acad. Sci. USA, 1978, 75(3):1314-1318.
McNutt, et al., Embryonic Stem Cell-Derived Neurons are a Novel, Highly Sensitive Tissue Culture Platform for Botulinum Research, Biochemical and Biophysical Research Communications, 2011, 405:85-90.
Morris, et al., Interaction of Fragments B and C of Tetanus Toxin with Neural and Thyroid Membranes and with Gangliosides, The Journal of Biological Chemistry, 1980, 255(13):6071-6076.
Nelson, et al., Synapse Formation Between Clonal Neuroblastoma X Glioma Hybrid Cells and Striated Muscle Cells, Proc. Nat. Acad. Sci. USA, 1976, 73(1):123-127.
Okamoto, et al., A Novel Octamer Binding Transcription Factor is Differentially Expressed in Mouse Embryonic Cells, Cell, 1990, 60(3):461-472.
Pellett, et al., A Neuronal Cell-Based Botulinum Neurotoxin Assay for Highly Sensitive and Specific Detection of Neutralizing Serum Antibodies, FEBS Letters, 2007, 581:4803-4808.
Pellett, et al., Comparison of the Primary Rat Spinal Cord Cell (RSC) Assay and the Mouse Bioassay for Botulinum Neurotoxin Type A Potency Determination, Journal of Pharmacological and Toxicological Methods, 2010, 61 (3):304-310.
Pellett, et al., Sensitive and Quantitative Detection of Botulinum Neurotoxin in Neurons Derived from Mouse Embryonic Stem Cells, Biochemical and Biophysical Research Communications, 2011, 404(1):388-392.
Pier, et al., Botulinum Neurotoxin Subtype A2 Enters Neuronal Cells Faster than Subtype A1, FEBS Letters, 2011, 585:199-206.
Pun, et al., Antisense Agrin cDNA Transfection Blocks Neuroblastoma Cell-Induced Acetylcholine Receptor Aggregation When Co-Cultured with Myotubes, Molecular and Cellular Neuroscience, 1997, 10(1-2):87-99.
Rasetti-Escargueil, et al., Enhanced Sensitivity to Botulinum Type A Neurotoxin of Human Neuroblastoma SH-SY5Y Cells After Differentiation Into Mature Neuronal Cells, The Botulinum Journal, 2011, 2(1):30-48.
Rogers, et al., High Affinity Binding of Tetanus Toxin to Mammalian Brain Membranes, The Journal of Biological Chemistry, 1981, 256(5):2402-2407.
Rummel, et al., The Hcc-Domain of Botulinum Neurotoxins A and B Exhibits a Singular Ganglioside Binding Site Displaying Serotype Specific Carbohydrate Interaction, Molecular Microbiology, 2004, 51(3):631-643.
Schantz, et al., Microbiological Methods: Standardized Assay for Clostridium Botulinum Toxins, Journal of the Association of Official Analytical Chemists, 1978, 61(1):96-99.
Shimazaki, et al., Hybrid Cell Extinction and Re-Expression of Oct-3 Function Correlates with Differentiation Potential, The EMBO Journal, 1993, 12(12):4489-4498.
Smith, et al., Sequence Variation Within Botulinum Neurotoxin Serotypes Impacts Antibody Binding and Neutralization, Infection and Immunity, 2005, 73(9):5450-5457.
Takahashi, et al., Retinoic Acid and Neurotrophins Collaborate to Regulate Neurogenesis in Adult-Derived Neural Stem Cell Cultures, J. Neurobiol., 1999, 38:65-81.
Turner, et al., Brn-3.2: A Brn-3-Related Transcription Factor with Distinctive Central Nervous System Expression and Regulation by Retinoic Acid, Neuron, 1994, 12(1):205-218.
Whitemarsh, et al., Novel Application of Human Neurons Derived from Induced Pluripotent Stem Cells for Highly Sensitive Botulinum Neurotoxin Detection, Toxicological Sciences, 2012, 126(2):426-435.

(56) References Cited

OTHER PUBLICATIONS

Wilson, et al., Defects in Synapse Formation and Acetylcholine Release by Neuroblastoma and Hybrid Cell Lines, Fed. Proc., 1978, 37:1784, #2819.

Yowler, et al., Botulinum Neurotoxin A Activity is Dependent Upon the Presence of Specific Gangliosides in Neuroblastoma Cells Expressing Synaptotagmin I, The Journal of Biological Chemistry, 2002, 277(36):32815-32819.

* cited by examiner

A.

Co-Cultured NG108-15 / C2C12

B.

COMPOSITIONS AND METHODS OF USING DIFFERENTIATED CELLS SENSITIZED TO BOTULINUM NEUROTOXIN

CROSS-REFERENCE TO RELATED APPLICATIONS

This application claims priority to U.S. Provisional Application Ser. No. 61/700,965 filed Sep. 14, 2012, which is incorporated herein by reference in its entirety.

STATEMENT REGARDING FEDERALLY SPONSORED RESEARCH OR DEVELOPMENT

This invention was made with government support under AI082826 and AI093504 awarded by the National Institutes of Health. The government has certain rights in the invention.

FIELD OF THE INVENTION

The present invention relates to methods of generating differentiated cells having neuron-like morphology and increased sensitivity to neurotoxin and methods of using such differentiated cells for detecting neurotoxin.

BACKGROUND OF THE INVENTION

Botulinum neurotoxin (BoNT) is a protease naturally produced in a pathogenic bacterial strain, *Clostridium botulinum*. Food borne botulism is primarily due to contamination of food by bacterial spores in an anaerobic environment. The bacteria require an anaerobic environment for the spores to germinate and for bacteria to grow. Botulism can be life threatening. The protein acts as a neurotoxin and is the most acutely toxic substance known to man. However, the toxin has legitimate medical uses for treating diseases including diseases associated with severe muscle spasms, hyperhidrosis, pain, and others as the toxin can inhibit nerve activity by blocking neurotransmitter transmission, thereby decreasing muscle activity. The most lucrative application of BoNT is cosmetic usage where companies again harness the toxin's ability to decrease muscle activity thereby smoothing wrinkles.

Botulinum neurotoxin is classified by the Centers for Disease Control and Prevention as one of the six highest-risk threat agents for bioterrorism ("Category A" bioterrorism agents). BoNT is a 150 kDa single chain protein which is linked by a disulfide bond that can be cleaved into a 100 kDa Heavy Chain (HC) and a 50 kDa Light chain (LC) by endogenous or exogenous proteases. The LC is a zinc metalloprotease which cleaves different SNARE proteins depending on the serotype causing flaccid paralysis. The HC consists of a C-terminal binding domain ($H_C$) which is responsible for receptor binding and a N-terminal translocation domain ($H_N$) which is responsible for delivering the catalytic light chain to the neuronal cytosol. Based on their ability to be neutralized by type specific antiserum, BoNTs have traditionally been categorized into seven serotypes (BoNT/A-G), among which BoNTs A, B, E, and F are known to cause human botulism.

An in vivo mouse bioassay is an FDA-approved method for detecting BoNT activity. See Hatheway et al., in Laboratory Diagnosis of Infectious Diseases: Principles and Practice. Springer-Verlag, New York, 1988, p. 111-133; Schantz and Kautter, *J. Assoc. Off. Anal. Chem.* 61:96-99 (1978). The mouse bioassay, which detects low pM amounts of BoNT/A, requires injecting mice intraperitoneally or intravenously with toxin or toxin/antibody mixtures and observing the injected mice for signs of toxicity and death. Another FDA-approved method for detecting BoNT activity is a cell-based assay using SiMa cells. See Fernández-Salas et al., *PLoS One* 7(11):e49516 (2012). For in vitro assays, continuous cell lines such as Neuro-2a, SK-N-SH, M17, SH-SY5Y, NT2, PC12, and SiMa have been tested for sensitivity to BoNT/A and are being used as research models. These cell lines, however, generally are insufficiently sensitive to compete with the mouse bioassay with the exception of differentiated SiMA cells (Fernández-Salas et al., supra). Accordingly, there remains a need for practical and highly sensitive compositions and methods for detecting botulinum neurotoxin and their neutralizing antibodies for clinical and research applications.

SUMMARY OF THE INVENTION

In a first aspect, the present invention provides a cell population sensitized to botulinum neurotoxin. The cell population can comprise differentiated NG108-15 cells obtained by culturing NG108-15 cells in a serum-free culture medium comprising retinoic acid or purmorphamine or any Sonic Hedgehog (Shh)-mimicking molecule for a time sufficient for the cells to exhibit a motor neuron-like morphology. The differentiated NG108-15 cells can be cholinergic and exhibit increased sensitivity to botulinum neurotoxin relative to undifferentiated NG108-15 cells. The NG108-15 cells can be cultured in the presence of a myotube. The myotube can be a differentiated C2C12 cell. The NG108-15 cells can be cultured in the presence of the myotube for at least 5 days. The NG108-15 cells can be cultured in the presence of a ganglioside, preferably GT1b. Differentiated NG108-15 cells can synthesize choline acetyltransferase (ChAT). The botulinum neurotoxin can be selected from the group consisting of botulinum neurotoxin serotype A (BoNT/A), botulinum neurotoxin serotype B (BoNT/B), botulinum neurotoxin serotype C (BoNT/C), botulinum neurotoxin serotype D (BoNT/D), botulinum neurotoxin serotype E (BoNT/E), botulinum neurotoxin serotype F (BoNT/F), and botulinum neurotoxin serotype G (BoNT/G), or any subtypes thereof.

In another aspect, the present invention provides a method of detecting botulinum neurotoxin or an antibody specific to botulinum neurotoxin in a sample. The method can comprise contacting a cell sensitized to botulinum neurotoxin to the sample; and detecting cleavage of a neurotoxin-specific cleavage substrate in the contacted cell, wherein cleavage of the cleavage substrate is indicative of botulinum neurotoxin in the sample. The method can comprise contacting a cell sensitized to botulinum neurotoxin to the sample; and detecting cleavage of a neurotoxin-specific cleavage substrate in the contacted cell, wherein cleavage of the cleavage substrate is indicative of an antibody specific to botulinum neurotoxin in the sample.

The neurotoxin-specific cleavage substrate can comprise a polypeptide selected from the group consisting of SNAP-25, VAMP/synaptobrevin, and syntaxin. Cleavage of SNAP-25 can be indicative of BoNT/A, BoNT/C, or BoNT/E in the sample. Cleavage of VAMP/synaptobrevin can be indicative of BoNT/B, BoNT/D, BoNT/F, or BoNT/G in the sample. Cleavage of syntaxin can be indicative of BoNT/C in the sample.

The sample can be a biological sample, preferably serum, blood, plasma, or tissue. The sample can be a food, medicament, or product for human consumption.

Figure 2:
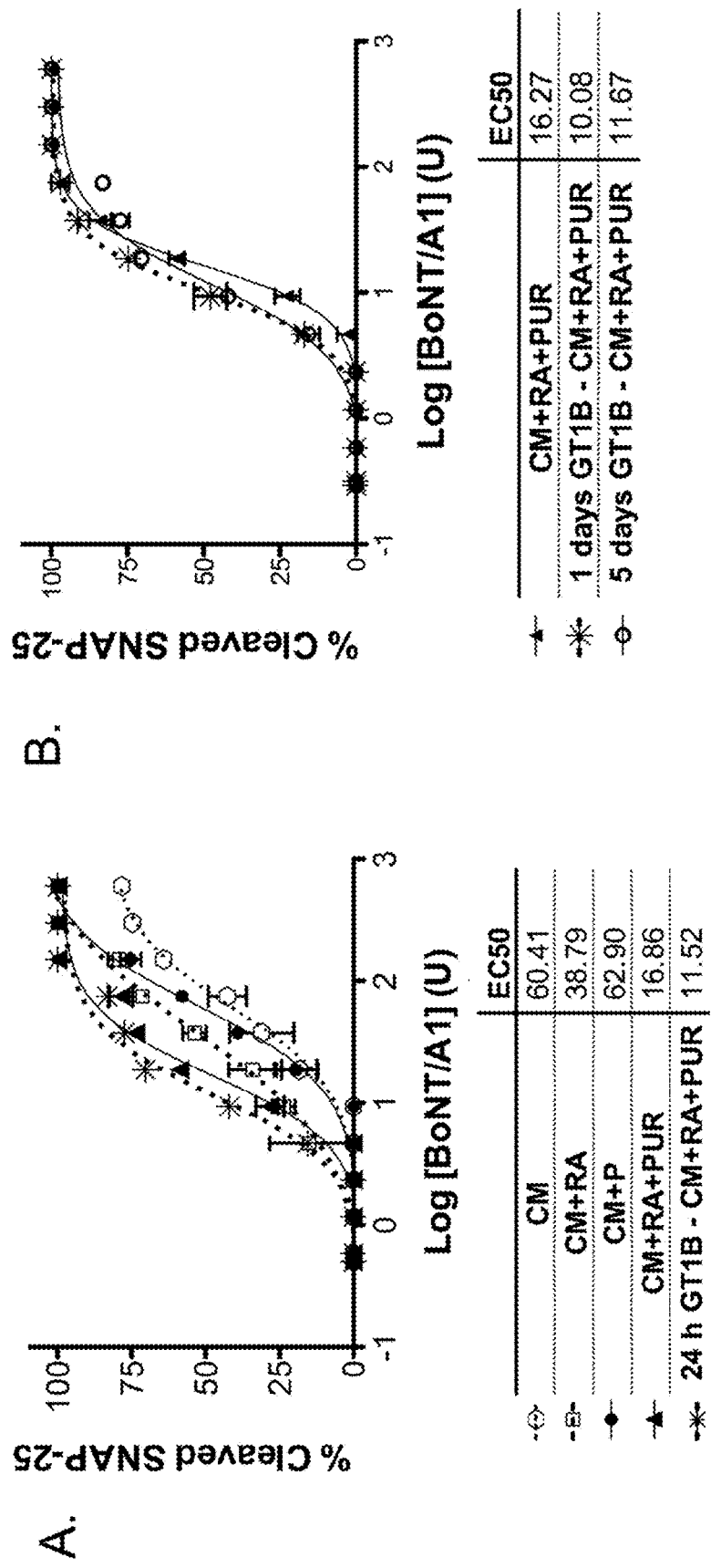

FIG. 2 presents data demonstrating NG108-15 cell sensitivity to BoNT/A1. (A) NG108-15 cells were differentiated for 5 days in CM (serum-free differentiation culture medium), CM+RA (all-trans retinoic acid), CM+PUR (purmorphamine), CM+RA+PUR, or GT1B-CM-RA-PUR (24 hour GT1B exposure) prior to BoNT/A1 addition. (B) NG108-15 cells were differentiated for 5 days in CM+RA+PUR and exposed to GT1B continuously for 5 days prior to BoNT/A1 addition.

Figure 3:
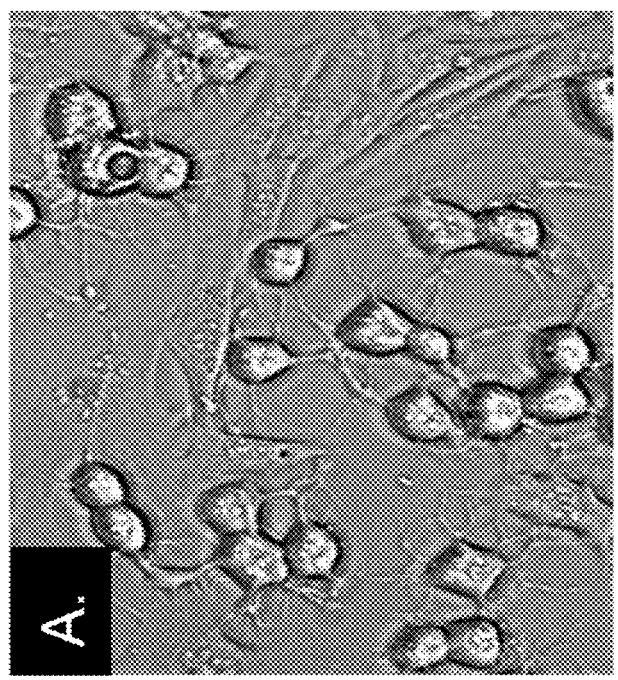
Figure 3:
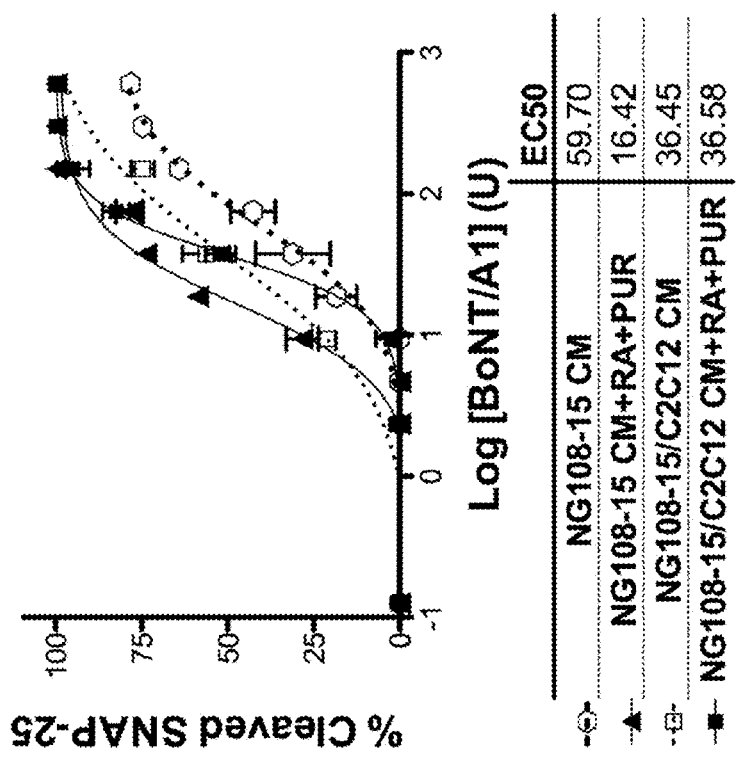

FIG. 3 presents data demonstrating NG108-15 cell sensitivity to BoNT/A1 following myotube co-culture. (A) Undifferentiated NG108-15 cells were co-cultured with differentiated C2C12 myotubes and differentiated for 5 days. Cells were visualized under phase-contrast using a Nikon Eclipse TE300 and photographed using a Photometrics Cool SNAP HQ camera. (B) Co-cultured cells were differentiated in CM or CM+RA+PUR prior to BoNT/A1 addition. All cells were exposed to the indicated toxin dilutions for 48 hours in parallel. Cell lysates were analyzed for SNAP-25 cleavage by Western blot. Data from three Western blots were quantified by densitometry, and data plots and $EC_{50}$ values were generated. The maturation time and $EC_{50}$ values are shown.

DETAILED DESCRIPTION OF THE INVENTION

The present invention is based at least in part on the present discovery that particular culture conditions promoted the differentiation of hybrid cells of the NG108-15 cancer cell line, the cells of which are a fusion of mouse neuroblastoma and rat glioma cells, into cells having a distinct motor neuron-like morphology. It was further discovered that the differentiated cells secreted acetylcholine in a similar manner to primary neuronal cells but responded poorly to botulinum neurotoxin. In particular, it was discovered that differentiation of NG108-15 cells in serum-free medium containing retinoic acid or purmorphamine dramatically increased sensitivity of the neurons to botulinum neurotoxin, whereas cancerous cell lines have traditionally shown low sensitivity to laboratory or pharmaceutical preparations of botulinum neurotoxin. Importantly, these data suggested to us that differentiated NG108-15 cells could be used to develop sensitive assays for detecting and quantifying botulinum neurotoxin.

The NG108-15 cell line is a chimeric fusion of mouse neuroblastoma and rat glioma cells, and closely mimics naturally occurring motor neurons. Jiang et al., *J. Biol. Chem.* 278:45435-45444 (2003). The cells are cholinergic, that is they secrete acetylcholine as their neurotransmitter. Previous work demonstrated that NG108-15 cells co-cultured with C2C12 cells (*Mus musculus* myoblast cell line) allowed for the formation of in vitro neuromuscular junctions. Choi et al., *Neurosci. Lett.* 236:167-170 (1997); Busis et al., *Brain Res.* 324:201-210 (1984); Pun and Tsim, *Mol. Cell. Neurosci.* 10:87-99 (1997). NG108-15 (ATCC® No. HB-12317) cells can be obtained from the American Type Culture Collection® (ATCC), an international repository of cells and other biological material.

In a first aspect, the present invention is directed to a cell population sensitized to botulinum toxin. In a preferred embodiment, the cell population sensitized to botulinum toxin comprises differentiated NG108-15 cells obtained by culturing NG108-15 cells in a culture medium comprising a sufficient amount of retinoic acid or purmorphamine, a small molecule activator of the Hedgehog signaling pathway, such that the cells have a motor-neuron-like morphology.

In a preferred embodiment, NG108-15 cells are differentiated under serum-free culture conditions. An exemplary basal serum-free culture medium is Neurobasal® medium (Invitrogen). In some cases, one or more supplements are added to a serum-free culture medium. Culture medium supplements can include, without limitation, amino acids, growth factors, and antibiotics (e.g., penicillin, streptomycin).

In some cases, undifferentiated NG108-15 cells are differentiated in a serum-free culture medium comprising retinoic acid (RA) or purmorphamine (PUR). In other cases, NG108-15 cells are differentiated in a serum-free culture medium comprising both retinoic acid and purmorphamine or another Sonic Hedgehog (Shh)-mimicking molecule including, for example, Shh itself. Preferably, a serum-free culture medium comprises between 0.1 µM-100 µM RA and/or between 0.25 µM-25.0 µM PUR. More preferably, a serum-free culture medium comprises between 0.5 µM-10 µM RA and/or between 0.75 µM-5 µM PUR. Most preferably, a serum-free culture medium comprises 5 µM RA, 2.5 µM PUR, or 5 µM RA+2.5 µM PUR. In some cases, undifferentiated NG108-15 cells are cultured in the presence of RA or PUR for 1, 2, 3, 4, 5, or more days. Preferably, NG108-15 cells are cultured in the presence of RA or PUR for at least 5 days.

To facilitate cell attachment, NG108-15 cells can be cultured on a plating substrate comprising extracellular matrix components. For example, NG108-15 cells can be cultured on poly-L-ornithine, collagen, laminin, or Matrigel™ (Becton-Dickinson). Matrigel™ is an undefined extracellular matrix substrate comprising laminin, collagen, growth factors, and other molecules.

When cultured under the conditions provided herein, NG108-15 cells differentiate into cells which exhibit a motor neuron-like morphology, secrete acetylcholine, and exhibit increased sensitivity to botulinum neurotoxin relative to undifferentiated NG108-15 cells. As described herein, undifferentiated NG108-15 cells can be cultured in serum-free culture medium comprising retinoic acid or purmorphamine for a time sufficient to observe a change in the morphology of the cells to a motor neuron-like morphology. Cells having a motor neuron-like morphology will exhibit a distinct cell body with a long axon and finger-like dendritic projections. Differentiated NG108-15 cells of the present invention also will be cholinergic, meaning that they secrete acetylcholine. Any appropriate method can be used to identify differentiated NG108-15 cells as cholinergic. For example, immunostaining with antibodies against choline acetyltransferase (ChAT) can be performed.

As described herein, differentiated NG108-15 cells of the present invention also exhibit increased sensitivity to botulinum neurotoxin relative to undifferentiated NG108-15 cells. In some cases, the differentiated NG108-15 cells described herein have increased sensitivity to botulinum neurotoxin serotypes known to cause botulism. For example, differentiated NG108-15 cells can exhibit increased sensitivity to botulinum neurotoxin serotype A (BoNT/A), botulinum neurotoxin serotype B (BoNT/B), botulinum neurotoxin serotype E (BoNT/E), or botulinum neurotoxin serotype F (BoNT/F), or a subtype thereof, relative to undifferentiated NG108-15 cells or PC12 cells. As used herein, the phrase "half maximal effective concentration ($EC_{50}$)" refers to the concentration of a toxin (e.g., neurotoxin) or other compound which induces a response halfway between the baseline and maximum after some specified exposure time. As used herein, the term "$LD_{50}$" refers to the median lethal dose of a toxin or other compound in mice. In some cases, differentiated NG108-15 cells detect BoNT/A with a half maximal effective concentration ($EC_{50}$) value as low as approximately 11 mouse $LD_{50}$ units ($LD_{50}$ U), which indicates that the differentiated cells are significantly more sensitive than undifferentiated NG108-15 cells or PC12 cells. $EC_{50}$ values for differentiated cells of the present invention are approximately 11 mouse $LD_{50}$ U to approximately 17 mouse $LD_{50}$ U (e.g., 11, 12, 13, 14, 15, 16, 17 $LD_{50}$ U).

In some cases, NG108-15 cells are cultured in the presence of a myotube. Myotubes are multinucleated cells that are formed when proliferating myoblasts exit the cell cycle, differentiate, and fuse. Exemplary myotubes for use according to the methods described herein are differentiated C2C12 cells. The C2C12 cell line is a primary line of mouse adherent myoblasts, the cells of which can differentiate into actin- and myosin-positive myotubes after 5 days in culture. See Burattini et al., *Eur. J. Histochem.* 48(3):223-234 (2004). As described herein, co-culture of the differentiated NG108-15 cells with C2C12 myotubes can significantly increase the sensitivity of NG108-15 cells for neurotoxin (e.g., BoNT/A).

In some cases, NG108-15 cells are pre-treated with gangliosides. For example, NG108-15 cells can be pre-treated with a triasialoganglioside receptor GT1b, a co-receptor for botulinum toxin. Purified gangliosides containing the "1b" substructure (i.e., having a NeuAca-2,8NeuAc group on an internal galactose residue) have been shown to directly support botulinum and tetanus toxin binding. See, for example, Rogers et al., *J. Biol. Chem.* 256:2402-2407 (1981); Morris et al., *J. Biol. Chem.* 255:6071-6076 (1980); Holmgren et al., *Eur. J. Biochem.* 106:371-379 (1980). As described herein, the addition of GT1b to the culture medium improves cellular sensitivity to the toxin. In an exemplary embodiment, NG108-15 cells are co-cultured with GT1b prior to contacting to a sample or prior to toxin exposure. For example, cells pretreated with exogenous GT1b can be 1.5 times (e.g., 1.1, 1.2, 1.3, 1.4, 1.5, 1.6, 1.7, 1.8, or more) more sensitive to botulinum neurotoxin (e.g., BoNT/A) than untreated cells, with $EC_{50}$ values of 11-12 and approximately 17 $LD_{50}$ U respectively.

In another aspect, the present invention provides cell-based assays for detecting the presence of botulinum neurotoxin or antibodies specific to botulinum neurotoxin in a sample. In an exemplary embodiment, a method of detecting botulinum neurotoxin or an antibody specific to botulinum neurotoxin comprises contacting cells sensitized to botulinum toxin to a sample. A parallel assay can be performed wherein cells sensitized to BoNT are contacted to a control sample.

As used herein, "control sample" refers to a sample comprising a known amount of a botulinum neurotoxin and, if applicable, a known amount of diluent. In some cases, the control sample is a negative control sample which contains no toxin. Control samples can be used to form a standard curve. The method can also comprise detecting cleavage of a cleavage substrate in the contacted cell. A cleavage substrate can be a polypeptide to which the botulinum neurotoxin specifically binds in the cell (e.g., SNAP-25 for BoNT/A, BoNT/C, and BoNT/E; VAMP/synaptobrevin for BoNT/B, BoNT/D, BoNT/F, and BoNT/G; syntaxin for BoNT/C).

In some cases, the methods provided herein can be used with samples of different types. For example, a sample can be a biological sample such as serum, blood, plasma, or tissue. In some cases, the sample is a food, medicament, or product for human consumption.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

Various exemplary embodiments of compositions and methods according to this invention are now described in the following non-limiting Examples. The Examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Differentiating NG108-15 Neurons

Cell Lines: Cryopreserved NG108-15 (HB-12317) and C2C12 (CRL-1772) cell lines were purchased from the American Type Culture Collection (ATCC). Both cell types were thawed according to manufacturer's instructions, and maintained in 1× Dulbecco's Modified Eagle's Medium (DMEM) (CellGro) with 4.5 g/L glucose, L-glutamine and sodium pyruvate supplemented with 10% (v/v) fetal bovine serum (FBS) (Invitrogen), 2% HAT supplement (Invitrogen), 100 units/mL penicillin, and 100 units/mL streptomycin (Invitrogen) at 37° C., 5% $CO_2$. For differentiation, NG108-15 cells were seeded into 96-well plates (Techno Plastic Products) coated with 0.01% poly-L-ornithine (Sigma) and 8.3 µg/cm² Matrigel™ (BD Biosciences) at a density of approximately 20,000 cells per well. The cells were differentiated in serum-free medium (Neurobasal® medium supplemented with 2% B-27® Supplement, 2 mM Glutamax™, 100 units/mL penicillin/streptomycin (all from Invitrogen)). To induce motor neuron differentiation, 5 µM all-trans retinoic acid (RA) (Stemgent) and 2.5 µM purmorphamine (PUR) (Cal-Biochem) was added to the serum-free medium, and cells were incubated in this medium for at least 5 days with medium changes every 2 days. Where indicated, NG108-15 cells were exposed to 50 µg/mL of bovine brain trisialoganglioside GT1b (SIGMA) for at least 24 hours prior to BoNT/A1 toxin exposure.

Co-culture of NG108-15 cells with C2C12 myotubes: For the co-culture, C2C12 cells were seeded into 96-well plates (Techno Plastic Products) coated with 0.01% poly-L-ornithine (Sigma) and 8.3 µg/cm² Matrigel™ (BD Biosciences) at a density of approximately 200 cells per well. Cells were differentiated to myotubes for 2 days in serum-free differentiation medium prior to the addition of NG108-15 cells. The co-culture was then allowed to differentiate in serum-free medium for at least 5 days prior to use. Retinoic acid and/or purmorphamine was added as indicated.

Botulinum Neurotoxin Preparation: Pure botulinum neurotoxin (BoNT) serotype A subtype 1 (150 kDa) was prepared from *C. botulinum* strain Hall A hyper as previously described (Malizio et al., *Methods Mol. Biol.* 145:27-39 (2000)). The toxin was dissolved in phosphate buffered saline (12.5 mM $NaH_2PO_4$, 75 mM NaCl), pH 7.4 and 40% glycerol, and stored at –20° C. until use. Activity of the BoNT/A1 preparation was determined by the mouse bioassay (Hatheway, in: Laboratory Diagnosis of Infectious Diseases: Principles and Practice. Springer-Verlag, New York, 1988, pp. 111-133; Schantz and Kautter, *J. Assoc. Off. Anal. Chem.* 61:96-99 (1978)), and specific toxicity was $1.25 \times 10^8$ mouse $LD_{50}$ U/mg.

In Vitro Neuronal Toxicity Assays: For all neuronal toxicity assays, differentiated NG108-15 cells or co-cultured C2C12/NG108-15 cells were exposed to toxin 4-8 days post-differentiation as indicated. Cells were exposed to the indicated concentrations of BoNT/A1 in 50 μl of serum-free medium. All dilutions were tested in a minimum of triplicate and a negative control without toxin was always included. After a 48 hour toxin exposure, the toxin solution was removed, and cells were lysed in 50 μl of 1× lithium dodecyl sulfate (LDS) sample buffer (Invitrogen). The cell lysates were analyzed by Western immunoblot for SNAP-25 cleavage (Synaptic Systems) as previously described. See Pellett et al., *FEBS Lett.* 581:4803-4808 (2007); Pellett et al., *J. Pharmacol. Toxicol. Methods* 61:304-310 (2010). Cleaved and un-cleaved SNAP-25 bands were quantified by densitometry using a Foto/Analyst FX system and TotalLab Quant software (Fotodyne). Data plots and $EC_{50}$ values (four parameters-variable slope) were generated using GraphPad PRISM 5 software.

Phase Contrast Microscopy: Differentiated and undifferentiated C2C12 and NG108-15 cells were visualized under phase-contrast using a Nikon Eclipse TE300 microscope and photographed using a Photometrics Cool SNAP HQ camera.

Figure 1:
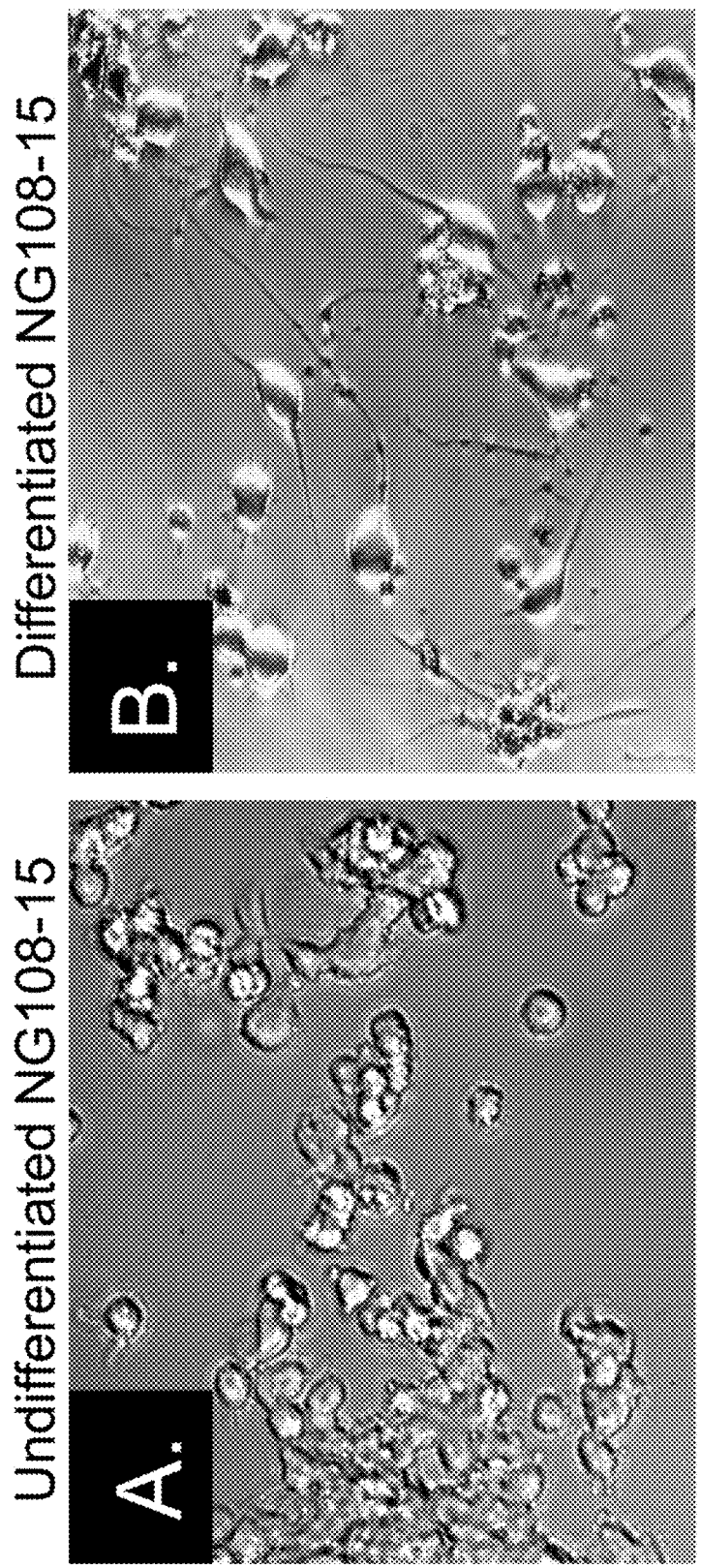
FIG. 1 presents images of (A) undifferentiated NG108-15 cells and (B) differentiated cells derived from the NG108-15 cell line. Cells were differentiated in serum-free medium containing retinoic acid and purmorphamine for 5 days. Visualized under phase-contrast using a Nikon Eclipse TE300 and photographed using a Photometrics Cool SNAP HQ camera.

Incubation in Serum-Free Medium Initiates Cellular Differentiation: Previous reports on NG108-15 cells differentiation described replacing the 20% FBS in the growth medium with 2% heat-inactivated horse serum. See, for example, Jiang et al., *J. Biol. Chem.* 278:45435-45444 (2003). However, applying this technique resulted in approximately 50% cell death and generated cells that required very high concentrations of BoNT/A1 to result in SNAP-25 cleavage (64,000-16,000 $LD_{50}$ U) (data not shown). In an attempt to improve differentiation conditions of the NG108-15 cells while creating cells with the greatest sensitivity to BoNT/A1 intoxication, the normal growth medium was removed entirely, and replaced with serum-free medium. The switch from serum-rich medium (FIG. 1A) to serum-free medium reduced cell death. The NG108-15 cells took on a very distinct motor neuron-like morphology consisting of dendrites, a soma, and an axon (FIG. 1B).

Example 2

BoNT/A Sensitivity of Differentiated NG108-15 Neurons

Retinoic Acid and Purmorphamine Improve Cellular Differentiation and Minimizes Cell Death In order to optimize a protocol for NG108-15 cell differentiation leading to greatest BoNT/A1 sensitivity, several differentiation conditions were tested. This included addition of 3.8 μM nerve growth factor (NGF), 0.2 μM cAMP, 5-0.5 μM all-trans retinoic acid (RA), and/or 2.5 μM purmorphamine (PUR) to the serum-free medium, as well as different plating matrices (poly-L-ornithine (PLO), collagen, laminin, matrigel) and differentiation periods from 1-10 days. The plating matrices did not affect BoNT/A sensitivity, however, the cells appeared the healthiest on plates coated with PLO and matrigel, and thus this coating procedure was chosen as the optimal pretreatment. While addition of NGF or cAMP to the medium did not affect BoNT/A1 sensitivity, the addition of RA and PUR significantly increased sensitivity in a dose dependent-fashion, with 5 μM RA resulting in the most sensitive cells.

To further optimize differentiation conditions with RA and PUR, cells were maintained in serum-free medium alone or medium containing either 5 μM RA, or 2.5 μM PUR, or both neuronal differentiation factors together for 1-5 days. Sensitivity to BoNT/A1 was then examined by exposing the cells to 2-fold dilutions of BoNT/A (600 $LD_{50}$ U-0.15 $LD_{50}$ U) in serum-free medium and assessing SNAP-25 cleavage via Western immunoblot after 48 hours. The cells differentiated in the presence of both RA and PUR for at least 5 days were most sensitive to BoNT/A1, with a SNAP-25 cleavage $EC_{50}$ value of ~17 $LD_{50}$ U. In contrast, cells that received only RA or PUR resulted in a significantly greater $EC_{50}$ values of ~39 $LD_{50}$ U and ~63 $LD_{50}$ U. Cells differentiated in only serum-free medium resulted in an $EC_{50}$ value of ~60 $LD_{50}$ U (FIG. 2A). Additionally, those cells differentiated in medium containing RA or PUR or both factors reached 100% cleavage of SNAP-25, while those cells in differentiation medium alone reached only approximately 80% cleavage at 600 $LD_{50}$ U (FIG. 2A).

Pretreatment of NG108-15 cells with GT1b Prior to Toxin Exposure Increases Sensitivity to BoNT/A1: Triasialoganglioside GT1b is a co-receptor that maximizes BoNT binding to cell surface receptors. Rummel et al., *Mol. Microbiol.* 51:631-643 (2004). Several cell lines (PC12, Neuro-2a, SH-SY5Y) demonstrate an increased sensitivity to BoNT/A1 when pre-loaded with trisialoganglioside GT1b for 24 hours prior to toxin exposure (Pier et al., *FEBS Lett.* 585:199-206 (2011); Yowler et al., *J. Biol. Chem.* 277:32815-32819 (2002); Rasetti-Escargueil et al., *Botulinum Journal* 2:30 (2011)). To determine if NG108-15 cells also show an increased sensitivity to BoNT/A1 after similar pre-treatment, cells previously differentiated in culture medium containing RA and PUR were exposed to 50 μg/ml of GT1b for 24 hours prior to BoNT/A exposure for 48 hours. GT1b-pretreated cells were approx. 1.5 times more sensitive to BoNT/A1 than untreated cells, with $EC_{50}$ values of about ~12 and ~17 $LD_{50}$ U respectively (FIG. 2A). To determine if sensitivity could be additionally increased by prolonged GT1b incubation, NG108-15 cells differentiated in medium containing 50 μg/ml of GT1b and RA and PUR for 5 days prior to BoNT/A1 intoxication, changing the medium every other day. The prolonged GT1b incubation did not further improve BoNT/A1 sensitivity (FIG. 2B).

Co-culturing NG108-15 with C2C12 Cells Increases NG108-15 Sensitivity to BoNT/A1: To determine how the formation of in vitro NMJs affects NG108-15 cells sensitivity to BoNT/A1, NG108-15 cells were co-cultured with pre-formed C2C12 myotubes for 5 days in serum-free medium before intoxication (FIG. 3A). Co-cultured NG108-15 formed visible connections with C2C12 myotubes via axon and dendrite extensions after 48 hours. Based on observations using light microscopy, the axon lengths of the NG108-15 cells were reduced in the co-culture as compared to the monoculture. The BoNT/A1 sensitivity of co-cultured cells (approx. 37 $LD_{50}$ U) was about 2-fold greater than that of non-co-cultured NG108-15 cells (approx. 60 $LD_{50}$ U) (FIG. 3B). Addition of the differentiation factors RA and PUR to the medium did not further increase the sensitivity nor improve the health of the co-cultured NG108-15 cells (approx. 37 $LD_{50}$ U).

As part of a screening effort to cell lines sensitive to BoNT/A1, the NG108-15 cell line, a chimeric fusion of mouse neuroblastoma and rat glioma cells, with motor neuron-like characteristic was examined. Because undifferentiated NG108-15 cells are relatively insensitive to BoNT detection ($EC_{50}$=approx. 1,600 $LD_{50}$ U), the effect of differentiation of the NG108-15 cells in the serum-free medium with and without the presence of neuronal differentiation factors was monitored. These conditions led to a relatively high sensitivity ($EC_{50}$=approx. 60 $LD_{50}$ U), however, about 50% of the cells died during this differentiation procedure, making it difficult to achieve consistent cultures of differentiated neurons. Thus, differentiation in the presence of factors known to drive motor neuron differentiation in stem cells (RA and PUR) (Johnson et al., *Development* 114:75-87 (1992); Okamoto et al., *Cell* 60:461-472 (1990); Shimazaki et al., *EMBO J.* 12:4489-4498 (1993); Fuji et al., *Neuron* 11:1197-1206 (1993); Turner et al., *Neuron* 12:205-218 (1994); Takahashi et al., *J. Neurobiol.* 38:65-81 (1999); Li et al., *Stem Cells* 26:886-893 (2008)) was examined. This increased sensitivity ~4-fold ($EC_{50}$=~16 $LD_{50}$ U). Taken together, these data indicate that differentiation of NG108-15 cells in serum-free medium supplemented with 5 μM RA and 2.5 μM PUR results in consistently healthy motor neuron-like cells (FIG. 2A) with the greatest BoNT/A sensitivity.

A 24-hour exposure to trisialoganglioside GT1b prior to intoxication resulted in an additional 1.5-fold increase in BoNT/A1 sensitivity, but a continuous exposure of 5 days did not further increase sensitivity (FIGS. 2A, B). Extracellular GT1b has been shown in neuro-2a cells to be incorporated into the cell membrane, leading to a dramatic increase in BoNT/A sensitivity due to increased association of the toxin with the cell membrane. Yowler et al., *J. Biol. Chem.* 277: 32815-32819 (2002). Similarly, the increase in sensitivity in NG108-15 cells after GT1b incubation is likely due to an increased ability of BoNT/A1 to associate with the cell membrane, and therefore undergo endocytosis. While significant, the relatively small GT1b-induced increase in BoNT/A1 sensitivity can likely be explained by an increase of endogenous gangliosides as the NG108-15 cells are differentiated. Dahms et al., *J. Neurosci.* 3:806-817 (1983). However, these data suggest that the cell surface becomes trisialoganglioside-saturated after the 24 hour incubation such that continuous GT1b incubation does not further improve toxin binding.

Because botulism is characterized by symptoms of specific motor neuron paralysis, these cells present an interesting model system to study BoNTs. Previous reports have shown that NG108-15 cells can be differentiated into cells with motor neuron like morphologies and characteristics including the secretion of acetylcholine and the synthesis of choline acetyltransferase (Wilson et al., *Federation Proceedings* 37:1784 (1978); McGee et al., *Proc. Natl. Acad. Sci. U.S.A.* 75:1314-1318 (1978)), the ability to readily form synapses with differentiated C2C12 cells (Nelson et al., *Proc. Natl. Acad. Sci. U.S.A.* 73:123-127 (1976)), and can conduct miniature end-plate potentials (MEPPs) (Higashida, *J. Physiol.* 397:209-222 (1988)). The BoNT/A1 sensitivity of such co-cultured cells (FIG. 3A) was examined, and was increased over 2-fold compared to non co-cultured cells (FIG. 3B). This increase in sensitivity is likely due to the uncharacterized, environmental factors provided by the myotubes. Surprisingly, co-culturing cells in serum-free medium containing RA and PUR did not increase sensitivity further, but this can likely be attributed to a decrease in overall cell health.

While the differentiated NG108-15 cells are 50 times less sensitive than primary rat spinal cord (RSC) cells or stem cell derived neurons ($EC_{50}$~0.3 $LD_{50}$ U) (McNutt et al., *Biochem. Biophys. Res. Commun.* 405:85-90 (2011); Pellett et al., *Biochem. Biophys. Res. Commun.* 404:388-392 (2011); Pellett et al., *FEBS Lett.* 581:803-4808 (2007); Whitemarsh et al., *Toxicol. Sci.* 126:426-435 (2012)), these cells are significantly more sensitive than cell lines previously tested. Unlike primary cells and stem cell derived neurons, these cells do not require laborious animal dissections or prolonged differentiation periods and significantly less knowledge of cellular reprogramming. Additionally, NG108-15 cells are easy to maintain and can be robustly and consistently differentiated using the protocol described herein. While pre-differentiated neurons derived from human-induced pluripotent stem cells are now available for purchase and are exquisitely sensitive to BoNTs (Whitemarsh et al., *Toxicol. Sci.* 126:426-435 (2012)), these cells are very expensive and thus not suitable for all projects involving BoNT research. Using differentiated NG108-15 cells for BoNT toxicity testing is significantly less expensive than using primary cells or hiPSC-derived neurons, and the sensitivity is sufficient for many research projects. In addition, the motor neuron like characteristics of this cell line and the ability to co-culture the neurons with myotubes to form NMJs make it an interesting BoNT study model.

We claim:

1. An isolated cell population having increased sensitivity to botulinum neurotoxin, wherein the cell population comprises differentiated NG 108-15 cells obtained by culturing undifferentiated NG108-15 cells in a serum-free culture medium comprising retinoic acid and an agonist of sonic hedgehog (SHH) signaling for a time sufficient for the cells to exhibit a differentiated, motor neuron-like morphology, and wherein the differentiated NG108-15 cells are cholinergic and exhibit increased sensitivity to botulinum neurotoxin relative to undifferentiated NG108-15 cells or NG108-15 cells differentiated in the absence of retinoic acid and the SHH signaling agonist.

2. The cell population of claim 1, wherein culturing further comprises culturing the undifferentiated NG108-15 cells in the presence of a myotube.

3. The cell population of claim 2, wherein the myotube is a differentiated C2C12 cell.

4. The cell population of claim 2, wherein the undifferentiated NG108-15 cells are cultured in the presence of the myotube for at least 5 days.

5. The cell population of claim 1, wherein culturing further comprises culturing the undifferentiated NG108-15 cells in the presence of a ganglioside.

6. The cell population of claim 5, wherein the ganglioside is GT 1 b.

7. The cell population of claim 1, wherein differentiated NG108-15 cells synthesize choline acetyltransferase (ChAT).

8. The cell population of claim 1, wherein the botulinum neurotoxin is selected from the group consisting of botulinum neurotoxin serotype A (BoNT/A), botulinum neurotoxin serotype B (BoNT/B), botulinum neurotoxin serotype C (BoNT/C), botulinum neurotoxin serotype D (BoNT/D), botulinum neurotoxin serotype E (BoNT/E), botulinum neurotoxin serotype F (BoNT/F), and botulinum neurotoxin serotype G (BoNT/G), or a subtype thereof.

9. The cell population of claim 1, wherein the agonist of SHH signaling is purmorphamine or SHH.

10. The cell population of claim 9, wherein the agonist is purmorphamine.

11. A method of detecting botulinum neurotoxin in a sample, where the method comprises
    (a) contacting a differentiated NG108-15 cell of claim 1 sensitized to botulinum neurotoxin to the sample; and
    (b) detecting cleavage of a neurotoxin-specific cleavage substrate in the contacted cell, wherein cleavage of the cleavage substrate is indicative of biologically active botulinum neurotoxin in the sample.

12. The method of claim 11, wherein the neurotoxin-specific cleavage substrate comprises a polypeptide selected from the group consisting of SNAP-25, VAMP/synaptobrevin, and syntaxin.

13. The method of claim 12, wherein cleavage of SNAP-25 is indicative of a toxin selected from BoNT/A, BoNT/C, and BoNT/E in the sample.

14. The method of claim 12, wherein cleavage of VAMP/synaptobrevin is indicative of BoNT/B, BoNT/D, BoNT/F, or BoNT/G in the sample.

15. The method of claim 12, wherein cleavage of syntaxin is indicative of BoNT/C in the sample.

16. The method of claim 11, wherein the sample is a biological sample.

17. The method of claim 16, wherein the biological sample comprises a material selected from serum, blood, plasma, and tissue.

18. The method of claim 11, wherein the sample is selected from a food, a medicament, and a product for human consumption.

\* \* \* \* \*